United States Patent
Lee et al.

(10) Patent No.: US 6,693,136 B1
(45) Date of Patent: Feb. 17, 2004

(54) FLUORENES AND ANTHRACENES THAT INHIBIT $P2X_3$ AND $P2X_{2/3}$ CONTAINING RECEPTORS

(75) Inventors: Chih-Hung Lee, Vernon Hills, IL (US); Meiqun Jiang, Gurnee, IL (US); Richard A. Perner, Gurnee, IL (US); Arthur Gomtsyan, Vernon Hills, IL (US); Erol K. Bayburt, Gurnee, IL (US); Guo Zhu Zheng, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/206,265

(22) Filed: Jul. 26, 2002

(51) Int. Cl.[7] .................. A61K 31/18; A61K 31/38; A61K 31/195
(52) U.S. Cl. .................. 514/603; 514/437; 514/443; 514/562; 514/602; 549/26; 549/27; 549/43; 549/44; 549/45; 549/46; 549/47; 549/48; 562/427; 564/81; 564/82; 564/83
(58) Field of Search .................. 514/437, 443, 514/562, 602, 603; 549/26, 27, 43, 44, 45, 46, 47, 48; 562/427; 564/81, 82, 83

(56) References Cited

U.S. PATENT DOCUMENTS 4,959,500 A  *  9/1990  Schleifstein .................. 564/82

OTHER PUBLICATIONS

Abbott et al. "The formalin test: scoring properties fo the first and second phases of the pain response in rats", Pain 60:91–102 (1995).
Berge, J. Pharmaceutical Sciences 66:1 et seq. (1977).
Bleehen, "The effects of adenine nucleotides on cutaneous afferent nerve activity", Br. J. Pharmacol 62:573–577 (1978).
Cesare et al, Drug Dev. Res. 50:S01–02 (2000).
Cockayne et al. Drug Dev. Res. 50:005 (2000).
Cook et al., "Distinct ATP receptors on pain–sensing and stretch–sensing neurons", Nature 387:505–508 (1997).
Driessen et al., "Modulation of neural noradrealine and ATP release by angiotensin II and prostaglandin $E_2$ in guinea–pig vas deferns", Naunyn Schmiedebergs Arch Pharmacol 350:618–625 (1994).
Namasivayam et al., "Purinergic sensory neurotransmission in the urinary bladder: an invitro study in the rat", Brit J. Urol Int. 84L:854–860 (1999).
Perry et al., "2,7–disubstituted amidofluorenone derivatives as inhibitors of human telomerase," J. Med. Chem. 42:2679–2684 (1999).
Prescott et al., Methods in Cell Biology, Academic Press, New York 14:33 et seq. (1976).
Witek et al., "New pesticides and intermediates, Part VII. Some Azaalkenyl derivatives of N–phenylurea and N–phenylcarbamic acid," Polish Journal of Chemistry 55:25892600 (1981).

* cited by examiner

Primary Examiner—Peter O'Sullivan
(74) Attorney, Agent, or Firm—Johanna M. Corbin

(57) ABSTRACT

Compounds of formula (I)

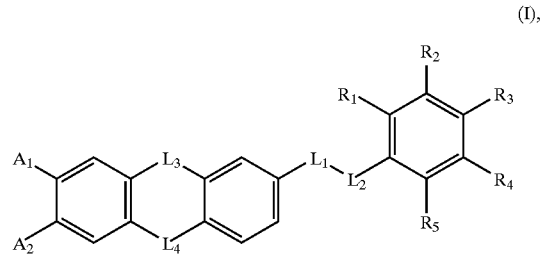

are novel $P2X_3$ and $P2X_2/P2X_3$ containing receptor antagonists and are useful in treating pain, urinary incontinence, and bladder overactivity.

25 Claims, No Drawings

FLUORENES AND ANTHRACENES THAT INHIBIT P2X$_3$ AND P2X$_{2/3}$ CONTAINING RECEPTORS

TECHNICAL FIELD

The present invention relates to compounds of formula (I), which are useful for treating diseases or conditions caused by or exacerbated by P2X receptor activity, pharmaceutical compositions containing compounds of formula (I) and methods of treatment using compounds of formula (I).

BACKGROUND OF THE INVENTION

P2X receptors function as homomultimeric cation-permeable ion channels and, in some cases, as heteromeric channels consisting of two different P2X receptor subtypes. At least one pair of P2X receptor subtypes, P2X$_2$ and P2X$_3$, functions as a heteromeric channel in rat nodose ganglion neurons where it exhibits distinct pharmacological and electrophysiological properties.

With respect to individual receptors, the rat P2X$_2$ containing receptor is expressed in the spinal cord, and in the nodose and dorsal root ganglia, while rat P2X$_3$ containing receptor expression is found primarily in a subset of neurons of the sensory ganglia. The distribution of both receptors is consistent with a role in pain transmission. The P2X$_2$ and P2X$_3$ subunits form functional channels when expressed alone, and can also form a functional heteromultimeric channel that has properties similar to currents seen in native sensory channels when co-expressed. Evidence from studies in rat nodose ganglia indicate that both P2X$_2$/P2X$_3$ heteromeric channels and P2X$_2$ homomeric channels contribute to adenosine triphosphate-induced currents.

ATP, which activates P2X$_2$, P2X$_3$, and P2X$_2$/P2X$_3$ containing receptors, functions as an excitatory neurotransmitter in the spinal cord dorsal horn and in primary afferents from sensory ganglia. ATP-induced activation of P2X receptors on dorsal root ganglion nerve terminals in the spinal cord stimulates the release of glutamate, a key neurotransmitter involved in nociceptive signaling. Thus, ATP released from damaged cells can evoke pain by activating P2X$_2$, P2X$_3$, or P2X$_2$/P2X$_3$ containing receptors on nociceptive nerve endings of sensory nerves. This is consistent with the induction of pain by intradermally applied ATP in the human blister-base model; the identification of P2X$_3$ containing receptors on nociceptive neurons in the tooth pulp; and with reports that P2X antagonists are analgesic in animal models. This evidence suggests that P2X$_2$ and P2X$_3$ function in nociception, and that modulators of these human P2X receptors are useful as analgesics.

It has been recently demonstrated that P2X$_3$ receptor gene disruption results in a diminished sensitivity to noxious chemical stimuli and reduced pain. P2X$_3$ containing receptor knock-out mice also exhibited a marked urinary bladder hyporeflexia upon cystometric evaluation, suggesting that P2X$_3$ antagonists have utility for treating bladder overactivity. P2X$_3$ knock-out mice had decreased voiding frequency, increased voiding volume, but normal bladder pressure. It has been proposed that ATP acts as a physiological regulator of sensory neurotransmission in visceral hollow organs such as bladder, and P2X$_3$ containing receptors localized on the basal surface of the urothelium. The urology data on the P2X$_3$ knock-out mice suggest that P2X$_3$ plays a major role in modulating the volume threshold for activation of micturition and that P2X$_3$ antagonists have therapeutic utility for urinary incontinence.

The nociceptive effects of exogenously administered ATP and P2X containing receptor agonists have also been demonstrated in laboratory animals. The peripheral nociceptive actions of P2X activation and stimulation of spinal P2X containing receptors also contribute to nociception as indicated by the ability of intrathecally (i.t.) administered P2 receptor agonists to increase sensitivity to acute and persistent noxious stimuli in rodents.

The utility of available purinergic ligands to evaluate the role of individual P2 receptor subtypes in mammalian physiology has been complicated by the susceptibility of P2 receptor agonists to undergo enzymatic degradation, and by the lack of P2 receptor subtype-selective agonists and antagonists.

Since subtype-selective ligands for the individual P2 receptors have yet to be identified, efforts to elucidate the specific P2X containing receptor subtypes involved in the transmission of nociceptive signals has been largely based on receptor localization and functional studies using immunohistochemical techniques. These studies have shown that both the homomeric P2X$_3$ and heteromeric P2X$_{2/3}$ containing receptor subtypes are selectively localized to the central and peripheral terminals of small diameter sensory neurons. Further, recent data has shown that P2X$_3$ specific immunoreactivity is significantly increased in both the injured dorsal root ganglion and in the ipsalateral spinal dorsal horn following chronic constriction injury of the rat sciatic nerve.

The functional and immunohistochemical localization of P2X$_3$ and/or P2X$_{2/3}$ containing receptors on sensory nerves indicates that these P2X containing receptors have a primary role in mediating the nociceptive effects of exogenous ATP. Thus, compounds which block or inhibit activation of P2X$_3$ containing receptors serve to block the pain stimulus. Antagonists of the P2X$_3$ homomeric channel and/or the P2X$_2$/P2X$_3$ heteromeric channel could successfully block the transmission of pain.

The compounds of the present invention are novel P2X$_3$ and P2X$_{2/3}$ antagonists, have utility in treating pain as well as in treating bladder overactivity and urinary incontinence.

SUMMARY OF THE INVENTION

The present invention discloses fluorene and anthracene compounds, a method for controlling pain in mammals, and pharmaceutical compositions including those compounds. More particularly, the present invention is directed to compounds of formula (I)

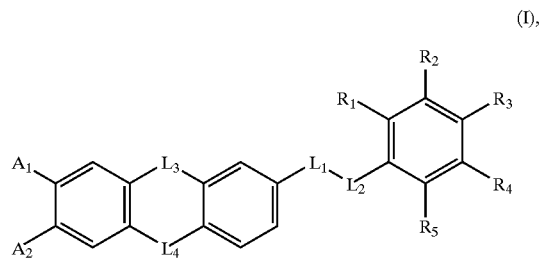

or a pharmaceutically acceptable salt, ester, amide, or prodrug thereof, wherein $A_1$ and $A_2$ are independently selected from hydrogen or

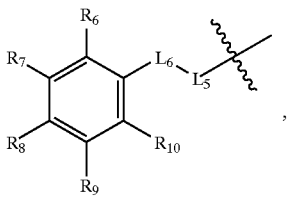, provided that one of $A_1$ and $A_2$ is hydrogen;

$L_1$ and $L_2$ are independently selected from $N(R_{11})$ or $S(O)_2$, provided that when $L_1$ is $N(R_{11})$ then $L_2$ is $S(O)_2$ or when $L_1$ is $S(O)_2$ then $L_2$ is $N(R_{11})$;

$L_3$ is selected from S, S(O), $S(O)_2$, C(O), $CH(OR_{12})$, $C(=NOR_{13})$, $C(=NNR_{12}R_{14})$, $C(=CHC(O)OR_{12})$, $CH_2$, or $CH_2CH_2$;

$L_4$ is selected from a covalent bond, C(O), $CH(OR_{12})$, $C(=NOR_{13})$, or $C(=NNR_{12}R_{14})$;

$L_5$ and $L_6$ are independently selected from $N(R_{15})$ or $S(O)_2$, provided that when $L_5$ is $N(R_{15})$ then $L_6$ is $S(O)_2$ or when $L_5$ is $S(O)_2$ then $L_6$ is $N(R_{15})$;

$R_1$, $R_2$, $R_3$, $R_4$, $R_5$, $R_6$, $R_7$, $R_8$, $R_9$, and $R_{10}$ are independently selected from hydrogen, alkenyl, alkoxy, alkoxycarbonyl, alkyl, alkylcarbonyl, alkylcarbonyloxy, halogen, haloalkoxy, haloalkyl, hydroxy, or $-NZ_1Z_2$ wherein $Z_1$ and $Z_2$ are independently selected from hydrogen, alkyl, or alkylcarbonyl;

$R_{11}$, $R_{12}$, $R_{14}$, and $R_{15}$ are independently selected from hydrogen and alkyl; and $R_{13}$ is selected from hydrogen, alkyl, or carboxyalkyl.

DETAILED DESCRIPTION OF THE PRESENT INVENTION

All references contained herein are fully incorporated by reference.

In the principle embodiment, compounds of formula (I) are disclosed

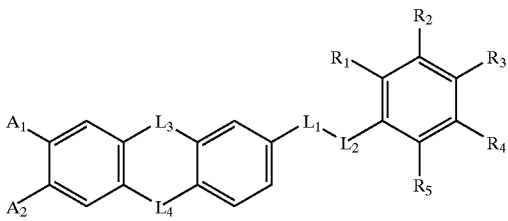

or a pharmaceutically acceptable salt, ester, amide, or pro-drug thereof, wherein $A_1$ and $A_2$ are independently selected from hydrogen or

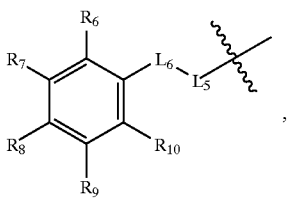, provided that one of $A_1$ and $A_2$ is hydrogen;

$L_1$ and $L_2$ are independently selected from $N(R_{11})$ or $S(O)_2$, provided that when $L_1$ is $N(R_{11})$ then $L_2$ is $S(O)_2$ or when $L_1$ is $S(O)_2$ then $L_2$ is $N(R_{11})$;

$L_3$ is selected from S, S(O), $S(O)_2$, C(O), $CH(OR_{12})$, $C(=NOR_{13})$, $C(=NNR_{12}R_{14})$, $C(=CHC(O)OR_{12})$, $CH_2$, or $CH_2CH_2$;

$L_4$ is selected from a covalent bond, C(O), $CH(OR_{12})$, $C(=NOR_{13})$, or $C(=NNR_{12}R_{14})$;

$L_5$ and $L_6$ are independently selected from $N(R_{15})$ or $S(O)_2$, provided that when $L_5$ is $N(R_{15})$ then $L_6$ is $S(O)_2$ or when $L_5$ is $S(O)_2$ then $L_6$ is $N(R_{15})$;

$R_1$, $R_2$, $R_3$, $R_4$, $R_5$, $R_6$, $R_7$, $R_8$, $R_9$, and $R_{10}$ are independently selected from hydrogen, alkenyl, alkoxy, alkoxycarbonyl, alkyl, alkylcarbonyl, alkylcarbonyloxy, halogen, haloalkoxy, haloalkyl, hydroxy, or $-NZ_1Z_2$ wherein $Z_1$ and $Z_2$ are independently selected from hydrogen, alkyl, or alkylcarbonyl;

$R_{11}$, $R_{12}$, $R_{14}$, and $R_{15}$ are independently selected from hydrogen or alkyl; and $R_{13}$ is selected from hydrogen, alkyl, or carboxyalkyl.

In another embodiment of the present invention, compounds of formula (I) are disclosed wherein $A_2$ is hydrogen; $A_1$ is

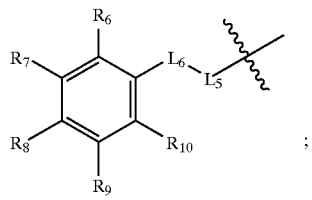;

$L_1$ and $L_5$ are $S(O)_2$; $L_2$ is $N(R_{11})$; $L_4$ is a covalent bond; $L_6$ is $N(R_{15})$; and $L_3$, $R_1$, $R_2$, $R_3$, $R_4$, $R_5$, $R_6$, $R_7$, $R_8$, $R_9$, $R_{10}$, $R_{11}$, and $R_{15}$ are as defined in formula (I).

In another embodiment of the present invention, compounds of formula (I) are disclosed wherein $A_2$ is hydrogen; $A_1$ is

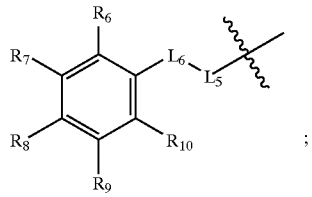;

$L_1$ and $L_5$ are $S(O)_2$; $L_2$ is $N(R_{11})$; $L_4$ is a covalent bond; $L_6$ is $N(R_{15})$; $R_1$, $R_3$, $R_4$, $R_5$, $R_6$, $R_8$, $R_9$, and $R_{10}$ are hydrogen; $R_2$ and $R_7$ are independently selected from hydroxy, alkoxy, or $-NZ_1Z_2$; $L_3$ is C(O); and $Z_1$, $Z_2$, $R_{11}$, and $R_{15}$ are as defined in formula (I).

In another embodiment of the present invention, compounds of formula (I) are disclosed wherein $A_2$ is hydrogen; $A_1$ is

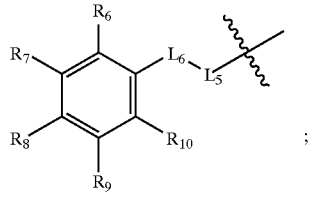;

$L_1$ and $L_5$ are $S(O)_2$; $L_2$ is $N(R_{11})$; $L_4$ is a covalent bond; $L_6$ is $N(R_{15})$; $R_1$, $R_3$, $R_4$, $R_5$, $R_6$, $R_8$, $R_9$, and $R_{10}$ are hydrogen; $R_2$ and $R_7$ are independently selected from hydroxy, alkoxy, or $-NZ_1Z_2$; $L_3$ is $C(=NOR_{13})$; and $Z_1$, $Z_2$, $R_{11}$, $R_{13}$, and $R_{15}$ are as defined in formula (I).

In another embodiment of the present invention, compounds of formula (I) are disclosed wherein $A_2$ is hydrogen; $A_1$ is

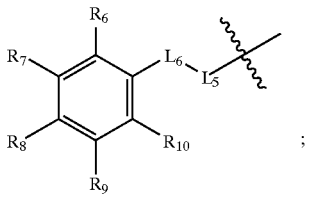

$L_1$ and $L_5$ are $S(O)_2$; $L_2$ is $N(R_{11})$; $L_4$ is a covalent bond; $L_6$ is $N(R_{15})$; $R_1$, $R_3$, $R_4$, $R_5$, $R_6$, $R_8$, $R_9$, and $R_{10}$ are hydrogen; $R_2$ and $R_7$ are independently selected from hydroxy, alkoxy, or $-NZ_1Z_2$; $L_3$ is $C(=NNR_{12}R_{14})$; and $Z_1$, $Z_2$, $R_{11}$, $R_{12}$, $R_{14}$, and $R_{15}$ are as defined in formula (I).

In another embodiment of the present invention, compounds of formula (I) are disclosed wherein $A_2$ is hydrogen; $A_1$ is

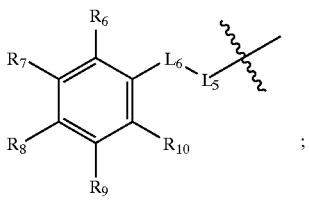

$L_1$ and $L_5$ are $S(O)_2$; $L_2$ is $N(R_{11})$; $L_4$ is a covalent bond; $L_6$ is $N(R_{15})$; $R_1$, $R_3$, $R_4$, $R_5$, $R_6$, $R_8$, $R_9$, and $R_{10}$ are hydrogen; $R_2$ and $R_7$ are independently selected from hydroxy, alkoxy, or $-NZ_1Z_2$; $L_3$ is $CH(OR_{12})$; and $Z_1$, $Z_2$, $R_{11}$, $R_{12}$, and $R_{15}$ are as defined in formula (I).

In another embodiment of the present invention, compounds of formula (I) are disclosed wherein $A_2$ is hydrogen; $A_1$ is

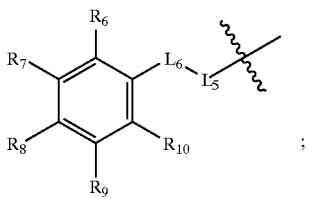

$L_1$ and $L_5$ are $S(O)_2$; $L_2$ is $N(R_{11})$; $L_4$ is a covalent bond; $L_6$ is $N(R_{15})$; $R_1$, $R_3$, $R_4$, $R_5$, $R_6$, $R_8$, $R_9$, and $R_{10}$ are hydrogen; $R_2$ and $R_7$ are independently selected from hydroxy, alkoxy, or $-NZ_1Z_2$; $L_3$ is $C(=CHC(O)OR_{12})$; and $Z_1$, $Z_2$, $R_{11}$, $R_{12}$, and $R_{15}$ are as defined in formula (I).

In another embodiment of the present invention, compounds of formula (I) are disclosed wherein $A_2$ is hydrogen; $A_1$ is

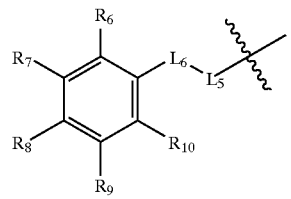

$L_1$ is $N(R_{11})$; $L_5$ is $N(R_{15})$; $L_2$ and $L_6$ are $-S(O)_2$; $L_4$ is a covalent bond; and $L_3$, $R_1$, $R_2$, $R_3$, $R_4$, $R_5$, $R_6$, $R_7$, $R_8$, $R_9$, $R_{10}$, $R_{11}$, and $R_{15}$ are as defined in formula (I).

In another embodiment of the present invention, compounds of formula (I) are disclosed wherein $A_2$ is hydrogen; $A_1$ is

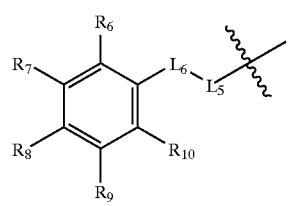

$L_1$ is $N(R_{11})$; $L_5$ is $N(R_{15})$; $L_2$ and $L_6$ are $-S(O)_2$; $L_4$ is a covalent bond; $R_1$, $R_3$, $R_4$, $R_5$, $R_6$, $R_8$, $R_9$, and $R_{10}$ are hydrogen; $R_2$ and $R_7$ are independently selected from hydroxy, alkoxy, or $-NZ_1Z_2$; $L_3$ is $C(O)$; and $Z_1$, $Z_2$, $R_{11}$, and $R_{15}$ are as defined in formula (I).

In another embodiment of the present invention, compounds of formula (I) are disclosed wherein $A_2$ is hydrogen; $A_1$ is

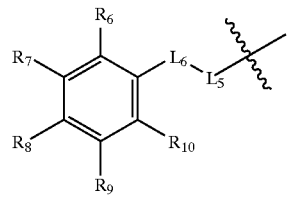

$L_1$ and $L_5$ are $S(O)_2$; $L_2$ is $N(R_{11})$; $L_6$ is $N(R_{15})$; $L_3$ and $L_4$ are independently selected from $C(O)$ or $C(=NOR_{13})$; $R_{13}$ is hydrogen; and $R_1$, $R_2$, $R_3$, $R_4$, $R_5$, $R_6$, $R_7$, $R_8$, $R_9$, $R_{10}$, $R_{11}$, and $R_{15}$ are as defined in formula (I).

In another embodiment of the present invention, compounds of formula (I) are disclosed wherein $A_2$ is hydrogen; $A_1$ is

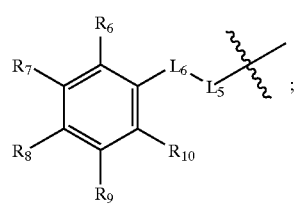

$L_1$ and $L_5$ are $S(O)_2$; $L_2$ is $N(R_{11})$; $L_6$ is $N(R_{15})$; $L_3$ and $L_4$ are independently selected from $C(O)$ or $C(=NOR_{13})$; $R_{13}$ is hydrogen; $R_1$, $R_3$, $R_4$, $R_5$, $R_6$, $R_8$, $R_9$, and $R_{10}$ are hydrogen; $R_2$ and $R_7$ are independently selected from hydroxy, alkoxy, or $-NZ_1Z_2$; and $Z_1$, $Z_2$, $R_{11}$, and $R_{15}$ are as defined in formula (I).

In another embodiment of the present invention, compounds of formula (I) are disclosed wherein $A_1$ is hydrogen; $A_2$ is

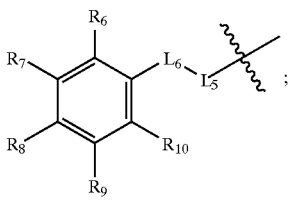

$L_1$ and $L_5$ are $S(O)_2$; $L_2$ is $N(R_{11})$; $L_6$ is $N(R_{15})$; $L_3$ and $L_4$ are independently selected from $C(O)$ or $C(=NOR_{13})$; $R_{13}$ is hydrogen; and $R_1$, $R_2$, $R_3$, $R_4$, $R_5$, $R_6$, $R_7$, $R_8$, $R_9$, $R_{10}$, $R_{11}$, and $R_{15}$ are as defined in formula (I).

In another embodiment of the present invention, compounds of formula (I) are disclosed wherein $A_1$ is hydrogen; $A_2$ is

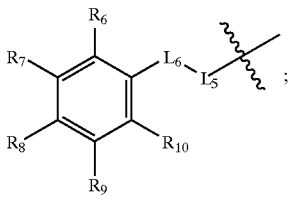

$L_1$ and $L_5$ are $S(O)_2$; $L_2$ is $N(R_{11})$; $L_6$ is $N(R_{15})$; $L_3$ and $L_4$ are independently selected from $C(O)$ or $C(=NOR_{13})$; $R_{13}$ is hydrogen; $R_1$, $R_3$, $R_4$, $R_5$, $R_6$, $R_8$, $R_9$, and $R_{10}$ are hydrogen; $R_2$ and $R_7$ are independently selected from hydroxy, alkoxy, or $-NZ_1Z_2$; and $Z_1$, $Z_2$, $R_{11}$, and $R_{15}$ are as defined in formula (I).

Another embodiment of the present invention relates to pharmaceutical compositions comprising a therapeutically effective amount of a compound of formula (I) or a pharmaceutically acceptable salt thereof in combination with a pharmaceutically acceptable carrier.

Another embodiment of the present invention relates to a method for treating pain in a mammal in need of such treatment comprising administering to the mammal a therapeutically effective amount of a compound of formula (I) or a pharmaceutically acceptable salt thereof in combination with a pharmaceutically acceptable carrier.

Another embodiment of the present invention relates to a method of treating urinary incontinence in a mammal in need of such treatment comprising administering a therapeutically effective amount of a compound of formula (I) or a pharmaceutically acceptable salt thereof.

Another embodiment of the present invention relates to a method of treating bladder overactivity in a mammal in need of such treatment comprising administering a therapeutically effective amount of a compound of formula (I) or a pharmaceutically acceptable salt thereof.

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "carbonyl" as used herein, means a $-C(O)-$ group.

The term "carboxy" as used herein, means a $-CO_2H$ group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "halo" or "halogen" as used herein, means $-Cl$, $-Br$, $-I$ or $-F$.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "hydroxy" as used herein, means an $-OH$ group.

Compounds of the present invention were named by ACD/ChemSketch version 5.0 (developed by Advanced Chemistry Development, Inc., Toronto, ON, Canada) or were given names which appeared to be consistent with ACD nomenclature.

Representative compounds of the present invention include, but are not limited to:

9-(hydroxyimino)-N,N'-bis(3-hydroxyphenyl)-9H-fluorene-2,7-disulfonamide;

{[(2,7-bis{[(3-hydroxyphenyl)amino]sulfonyl}-9H-fluoren-9-ylidene)amino]oxy}acetic acid;

9-hydroxy-N,N'-bis(3-hydroxyphenyl)-9H-fluorene-2,7-disulfonamide;

9-hydrazono-N,N'-bis(3-hydroxyphenyl)-9H-fluorene-2,7-disulfonamide;

(2,7-bis{[(3-hydroxyphenyl)amino]sulfonyl}-9H-fluoren-9-ylidene)acetic acid;

N-(3-{[(9-(hydroxyimino)-7-{[(3-hydroxyphenyl)amino]sulfonyl}-9H-fluoren-2-yl)sulfonyl]amino}phenyl)acetamide;

N-(3-aminophenyl)-9-(hydroxyimino)-N'-(3-hydroxyphenyl)-9H-fluorene-2,7-disulfonamide;

9-(hydroxyimino)-N,N'-bis(3-hydroxyphenyl)-N-methyl-9H-fluorene-2,7-disulfonamide;

N,N'-bis(3-hydroxyphenyl)-9-(methylhydrazono)-9H-fluorene-2,7-disulfonamide;

N,N'-bis(3-hydroxyphenyl)-9,10-dioxo-9,10-dihydro-2,7-anthracenedisulfonamide;

10-(hydroxyimino)-N,N'-bis(3-hydroxyphenyl)-9-oxo-9,10-dihydro-2,7-anthracenedisulfonamide;

9,10-bis(hydroxyimino)-N,N'-bis(3-hydroxyphenyl)-9,10-dihydro-2,7-anthracenedisulfonamide;

N,N'-bis(3-hydroxyphenyl)-9,10-dioxo-9,10-dihydro-2,6-anthracenedisulfonamide;

10-(hydroxyimino)-N,N'-bis(3-hydroxyphenyl)-9-oxo-9,10-dihydro-2,6-anthracenedisulfonamide;

9,10-bis(hydroxyimino)-N,N'-bis(3-hydroxyphenyl)-9,10-dihydro-2,6-anthracenedisulfonamide;

3-methoxy-N-(7-{[(3-methoxyphenyl)sulfonyl]amino}-9-oxo-9H-fluoren-2-yl)benzenesulfonamide;

3-hydroxy-N-(7-{[(3-hydroxyphenyl)sulfonyl]amino}-9-oxo-9H-fluoren-2-yl)benzenesulfonamide; and 3-hydroxy-N-(9-(hydroxyimino)-7-{[(3-hydroxyphenyl)sulfonyl]amino}-9H-fluoren-2-yl)benzenesulfonamide; or pharmaceutically acceptable salts, amides, esters, or prodrugs thereof.

Abbreviations

Abbreviations which have been used in the descriptions of the Schemes and the Examples that follow are: DMSO for dimethylsulfoxide; HPLC high pressure liquid chromatography; and THF for tetrahydrofuran.

Preparation of Compounds of the Present Invention

The compounds and processes of the present invention will be better understood in connection with the following synthetic Schemes and Examples which illustrate a means by which the compounds of the present invention can be prepared.

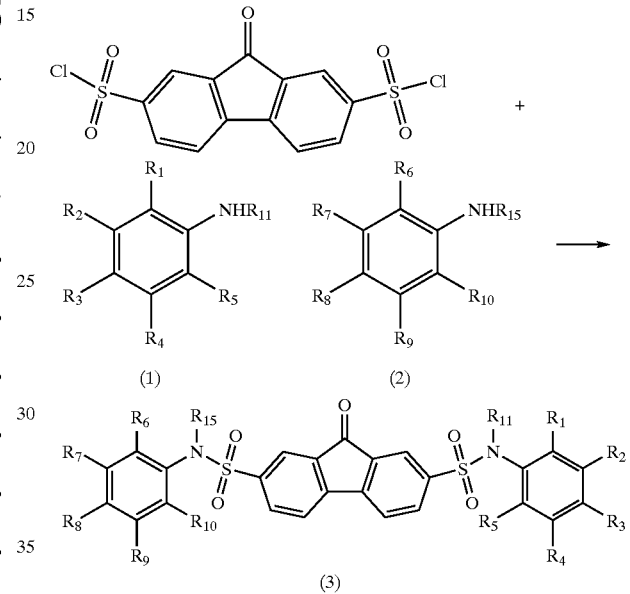

Fluorenes of general formula (3), wherein $R_1$, $R_2$, $R_3$, $R_4$, $R_5$, $R_6$, $R_7$, $R_8$, $R_9$, $R_{10}$, $R_{11}$, and $R_{15}$ are as defined in formula (I), can be prepared as described in Scheme 1. 9-Oxo-9H-fluorene-2,7-disulfonyl dichloride, purchased from Maybridge, can be treated with anilines of general formula (I) and (2) to provide fluorenes of general formula (3).

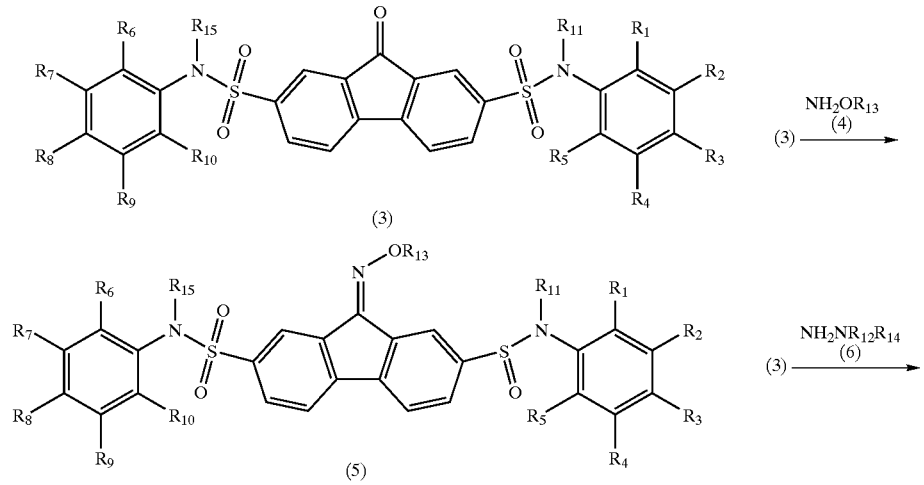

-continued

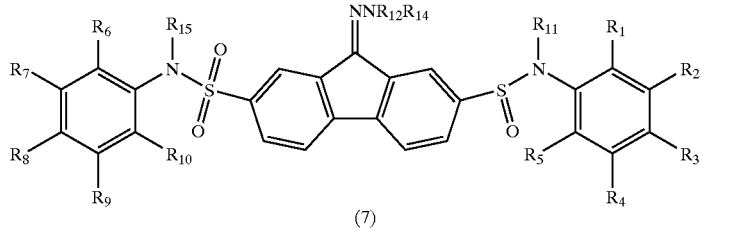

(7)

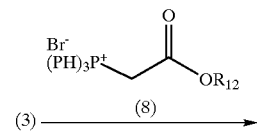

(3) $\xrightarrow{(8)}$

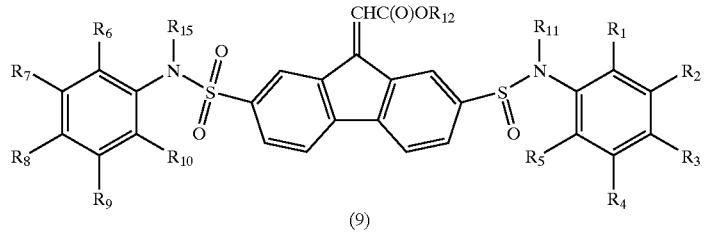

(9)

Fluorenes of general formula (5), (7), and (9), wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ are as defined in formula (I), can be prepared as described in Scheme 2. Fluorenes of general formula (3) can be treated with amines of general formula (4) and a catalytic amount of acid in an alcoholic solvent such as, but not limited to, ethanol with heat to provide fluorenes of general formula (5).

Fluorenes of general formula (3) can be treated with hydrazines of general formula (6) and a catalytic amount of acid in an alcoholic solvent such as, but not limited to, ethanol with heat to provide fluorenes of general formula (7).

Fluorenes of general formula (3) can be treated with phosphonium reagents of general formula (8) under standard Wittig conditions to provide fluorenes of general formula (9). Fluorenes of general formula (3) can also be treated with phosphonates under standard Homer-Wadsworth-Emmons conditions to provide fluorenes of general formula (9).

Scheme 3

-continued

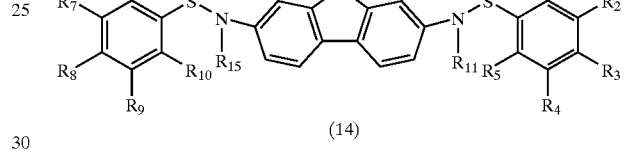

(14)

Fluorenes of general formula (14), wherein $R_1$, $R_2$, $R_3$, $R_4$, $R_5$, $R_6$, $R_7$, $R_8$, $R_9$, $R_{10}$, $R_{11}$, and $R_{15}$ are as defined in formula (I), can be prepared as described in Scheme 3. Fluorenes of general formula (11), prepared as described in P. J. Perry, M. A. Read, R. T. Davies, S. M. Gowan, A. P. Reszka, A. A. Wood, L. R. Kelland, S. Neidle, J. Med. Chem. 1999, 42, 2679, can be treated with sulfonyl chlorides of general formula (12) and (13) in a solvent or cosolvent such as, but not limited to, THF and pyridine to provide fluorenes of general formula (14).

Scheme 4

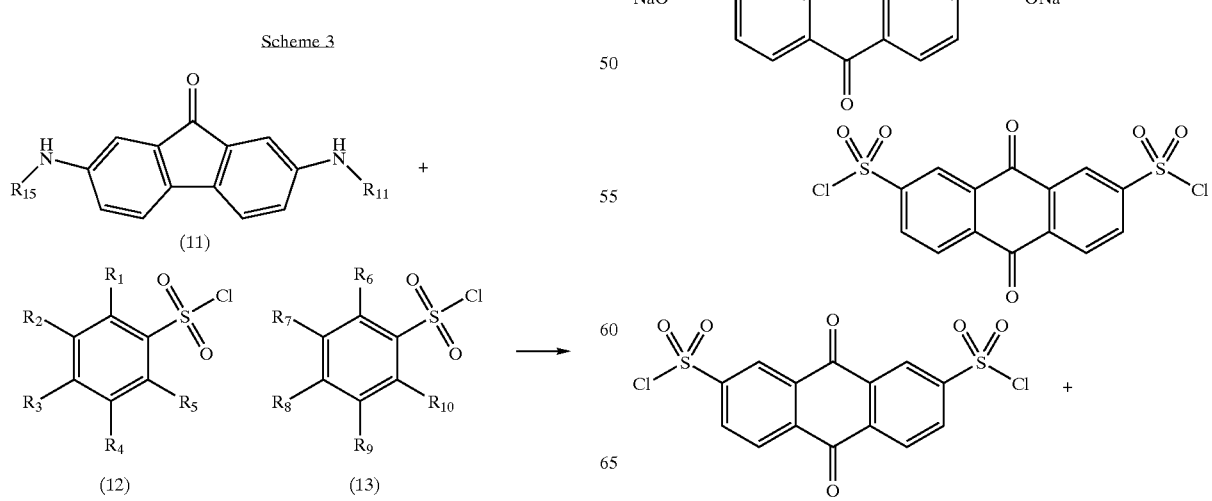

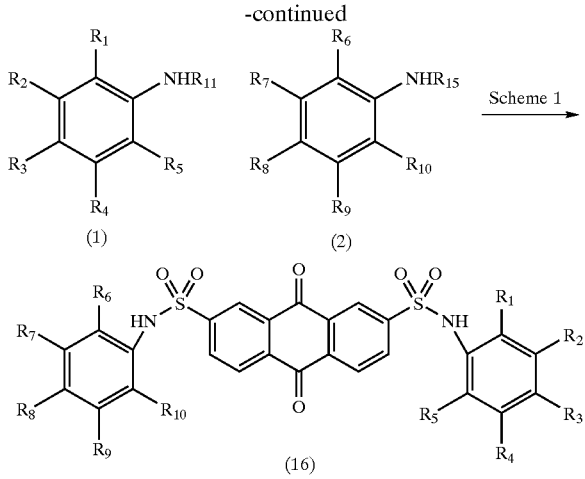

Anthracenes of general formula (16), wherein $R_1$, $R_2$, $R_3$, $R_4$, $R_5$, $R_6$, $R_7$, $R_8$, $R_9$, and $R_{10}$ are as defined in formula (I), can be prepared as described in Scheme 4. Anthraquinone-2,7-disulfonic acid disodium salt, can be treated with phosphorous oxychloride to provide anthracenedisulfonyl dichloride. Anthracenedisulfonyl dichloride can be treated with anilines of general formula (1) and (2) to provide anthracenes of general formula (16).

Anthraquinone-2,6-disulfonic acid disodium salt can be treated as described in Scheme 4 to provide 2,6-disubstituted anthracenes.

Anthracenes of general formula (16) can be treated as described in Scheme 2 to provide oximes, hydrazones, α,β unsaturated esters, or α,β unsaturated acids.

The following Examples are intended as an illustration of and not a limitation upon the scope of the invention as defined in the appended claims.

EXAMPLE 1

9-(Hydroxyimino)-N,N'-bis(3-hydroxyphenyl)-9H-fluorene-2,7-disulfonamide

Example 1A

N,N'-bis(3-Hydroxyphenyl)-9-oxo-9H-fluorene-2,7-disulfonamide

3-Aminophenol (0.91 g, 8.38 mmol) in pyridine was treated with 9-oxo-9H-fluorene-2,7-disulfonyl dichloride (1.58 g, 4.19 mmol, purchased from Maybridge) in one portion at 0° C. After two hours, the volatiles were removed at reduced pressure and the residue was partitioned between ethyl acetate and $H_2O$. The organic layer was separated, washed with 1N HCl, brine, dried ($Na_2SO_4$), filtered, and the filtrate concentrated under reduced pressure. The residue was purified by flash chromatography (8% $CH_3OH/CH_2Cl_2$) to provide the title compound as a yellow solid (1.97 g, 90% yield). $^1H$ NMR (300 MHz, DMSO-$d_6$) δ 10.31 (s, 2H), 9.50 (s, 2H), 7.97–8.11 (m, 4H), 7.92 (d, 2H), 7.0 (t, 2H), 6.49–6.64 (m, 4H), 6.43 (m, 2H); MS (DCI/$NH_3$) 540 $(M+NH_4)^+$.

EXAMPLE 1B 9-(Hydroxyimino)-N,N'-bis(3-hydroxyphenyl)-9H-fluorene-2,7-disulfonamide The product from Example 1A (1.35 g, 2.58 mmol) in absolute ethanol (20 mL) was treated with hydroxylamine hydrochloride (0.20 g, 2.84 mmol) and two drops of concentrated HCl and heated at reflux for 5 hours. The mixture was allowed to cool to room temperature and concentrated under reduced pressure. The residue was dissolved in ethyl acetate, washed with saturated $NaHCO_3$ solution, brine, dried ($Na_2SO_4$), filtered, and the filtrate was concentrated under reduced pressure. The residue was solidified by addition of 5% $CH_3OH/CH_2Cl_2$ then collected by filtration and dried under reduced pressure to provide the title compound as a white solid (0.92 g, 66% yield). $^1H$ NMR (500 MHz, DMSO-$d_6$) δ 13.29 (bs, 1H), 10.21 (m, 2H), 9.40 (m, 2H), 8.75 (m, 1H), 8.02–8.15 (m, 3H), 7.80–7.90 (m, 2H), 6.96 (m, 2H), 6.57 (m, 2H), 6.52 (m, 2H), 6.40 (m, 2H); MS (ESI) 536 $(M-H)^-$; Anal calcd for $C_{25}H_{19}N_3O_7S_2$: C, 55.86; H, 3.56; N, 7.82. Found: C, 55.64; H, 3.71; N, 7.61.

EXAMPLE 2

{[(2,7-bis{[(3-Hydroxyphenyl)amino]sulfonyl}-9H-fluoren-9-ylidene)amino]oxy}acetic Acid The product from Example 1A in pyridine (3 mL) was treated with carboxymethoxylamine hemihydrochloride (93 mg, 0.43 mmol) and heated at reflux. After 30 minutes, the solution was allowed to cool to ambient temperature and the volatiles were removed at reduced pressure. The residue was partitioned between ethyl acetate and concentrated $NH_4Cl$. The organic layer was separated, washed with brine, dried ($Na_2SO_4$), filtered, and the filtrate concentrated under reduced pressure. The residue was triturated with $CH_2Cl_2$, collected by filtration, and dried under reduced pressure to provide the title compound as a white solid (128 mg, 56% yield). $^1H$ NMR (300 MHz, DMSO-$d_6$) δ 10.1–10.4 (bs, 2H), 9.4–9.6 (bs, 1H), 8.95 (m, 1H), 8.02–8.17 (m, 3H), 7.93 (m, 1H), 7.80 (m, 1H), 6.90–7.02 (m, 2H), 6.82 (m, 1H), 6.67–6.58 (m, 5H), 4.74 (s, 2H); MS (ESI) 594 $(M-H)^-$.

EXAMPLE 3

9-Hydroxy-N,N'-bis(3-hydroxyphenyl)-9H-fluorene-2,7-disulfonamide

The product from Example 1A (213 mg, 0.41 mmol) in absolute ethanol (5 mL) at 0° C. was treated cautiously with $NaBH_4$ (46 mg, 1.22 mmol). After 2 hours, the mixture was quenched with 1N HCl and diluted with ethyl acetate. The organic layer was separated, washed with saturated $NaHCO_3$ solution, brine, dried ($Na_2SO_4$), filtered, and concentrated under reduced pressure to provide the title compound as a white solid (154 mg, 72% m yield). $^1H$ NMR (300 MHz, DMSO-$d_6$) δ 10.22 (s, 2H), 9.43 (s, 2H), 7.95–8.05 (m, 4H), 7.80 (dd, 2H), 6.96 (t, 2H), 6.5–6.61 (m, 4H), 6.39 (m, 2H), 6.26 (d, 1H), 5.61 (d, 1H); MS (ESI) 523 $(M-H)^-$.

EXAMPLE 4

9-Hydrazono-N,N'-bis(3-hydroxyphenyl)-9H-fluorene-2,7-disulfonamide

EXAMPLE 4A tert-Butyl 2-(2,7-bis{[(3-Hydroxyphenyl)amino]sulfonyl}-9H-fluoren-9-ylidene)hydrazinecarboxylate The product from Example 1A (317 mg, 0.60 mmol) in ethanol (10 mL) was treated with $H_2NNHBoc$ (87 mg, 0.66 mmol) and a catalytic amount of p-toluenesulfonic acid. The mixture was heated at reflux for 3 hours, allowed to cool to room temperature, and concentrated under reduced pressure. The residue was purified by flash chromatography eluting with 8% $CH_3OH/CH_2Cl_2$ to provide the title compound as a yellow solid (241 mg, 63% yield). $^1$H NMR (300 MHz, DMSO-$d_6$) δ 11.29 (bs, 1H), 10.28 (bs, 2H), 9.45 (d, 2H), 8.52 (bs, 1H), 8.04–8.18 (m, 3H), 7.87 (m, 1H), 7.81 (m, 1H), 6.98 (m, 2H), 6.5–6.6 (m, 4H), 6.4 (m, 2H), 1.59 (s, 9H); MS (ESI) 635 (M–H)$^-$.

EXAMPLE 4B

9-Hydrazono-N,N'-bis(3-hydroxyphenyl)-9H-fluorene-2,7-disulfonamide

The product from Example 4A (218 mg, 0.34 mmol) in absolute ethanol was treated with three crystals of p-toluenesulfonic acid and heated at reflux. After 3 hours, the mixture was allowed to cool to room temperature and was concentrated under reduced pressure. The residue was taken up in ethyl acetate, washed with saturated $NaHCO_3$ solution, brine, dried ($Na_2SO_4$), filtered, and the filtrate was concentrated under reduced pressure. The residue was purified by flash chromatography (85% ethyl acetate/hexanes) to provide the title compound as a yellow solid (36 mg, 20% yield). $^1$H NMR (300 MHz, DMSO-$d_6$) δ 9.41 (d, 2H), 8.78 (bs, 2H), 8.63 (bs, 1H), 8.28 (d, 1H), 8.02–8.1 (m, 2H), 7.81 (dd, 1H), 7.70 (dd, 1H), 6.91–7.01 (m, 2H), 6.49–6.61 (m, 4H), 6.33–6.42 (m, 2H); MS (ESI) 535 (M–H)$^-$.

EXAMPLE 5

(2,7-bis{[(3-Hydroxyphenyl)amino]sulfonyl}-9H-fluoren-9-ylidene)acetic Acid

EXAMPLE 5A

Ethyl (2,7-bis{[(3-Hydroxyphenyl)amino]sulfonyl}-9H-fluoren-9-ylidene)acetate (Carbethoxymethyl)triphenyl-phosphonium bromide (3.73 g, 8.69 mmol) in dry 1,4-dioxane was treated with potassium tert-butoxide (0.98 g, 8.69 mmol). After stirring for 90 minutes, the mixture was treated with the product from Example 1A (0.83 g, 1.58 mmol). After stirring for 5 hours, the mixture was treated with water and extracted with ethyl acetate. The organic phase was separated, washed with brine, dried ($Na_2SO_4$), filtered, and the filtrate concentrated under reduced pressure. The residue was purified by flash chromatography (70% ethyl acetate/hexanes) to provide the title compound (0.47 g, 50% yield). $^1$H NMR (300 MHz, DMSO-$d_6$) δ 9.44 (d, 2H), 9.18 (d, 1H), 8.44 (d, 1H), 8.10 (m, 2H), 7.87 (m, 2H), 7.23 (s, 1H), 6.98 (m, 2H), 6.5–6.63 (m, 4H), 6.39 (m, 2H), 4.35 (q, 2H), 1.35 (t, 3H); MS (ESI) 591 (M–H)$^-$.

EXAMPLE 5B (2,7-bis{[(3-Hydroxyphenyl)amino]sulfonyl}-9H-fluoren-9-ylidene)acetic Acid The product from Example 5A (460 mg, 0.78 mmol) in THF (5 mL) and 15% aqueous NaOH (5 mL) was heated at reflux for 6 hours. The mixture was allowed to cool to ambient temperature, acidified, and extracted with ethyl acetate. The organic phase was separated, washed with brine, dried ($Na_2SO_4$), filtered, and the filtrate concentrated under reduced pressure to provide the title compound as a yellow solid (95 mg, 22% yield). $^1$H NMR (300 MHz, DMSO-$d_6$) δ 10.26 (s, 1H), 10.16 (s, 1H), 9.43 (s, 1H), 9.18 (d, 1H), 8.37 (d, 1H), 8.1 (m, 2H), 7.86 (m, 2H), 7.2 (s, 1H), 7.0 (t, 2H), 6.53–6.63(m, 4H), 6.42 (m, 2H). MS (ESI) 563 (M–H)$^-$.

EXAMPLE 6

N-(3-{[(9-(Hydroxyimino)-7-{[(3-hydroxyphenyl)amino]sulfonyl}-9H-fluoren-2-yl)sulfonyl]amino}phenyl)acetamide

EXAMPLE 6A

N-(3-{[(7-{[(3-Hydroxyphenyl)amino]sulfonyl}-9-oxo-9H-fluoren-2-yl)sulfonyl]amino}phenyl)acetamide 3-Aminophenol (0.29 g, 2.65 mmmol) and N-(3-aminophenyl)acetamide (0.49 g, 2.65 mmol) in pyridine were treated with 9-oxo-9H-fluorene-2,7-disulfonyl dichloride (1.00 g, 2.65 mmol) in one portion at 0° C. The mixture was allowed to warm to ambient temperature and stirred for 1 hour after which the volatiles were evaporated under reduced pressure. The residue was partitioned between ethyl acetate and $H_2O$. The separated organic phase was washed with 1N HCl, brine, dried ($Na_2SO_4$), filtered, and the filtrate concentrated under reduced pressure. The residue was purified by flash chromatography (85% ethyl acetate/hexanes) to provide the title compound as a yellow solid (577 mg, 39% yield). $^1$H NMR (300 MHz, DMSO-$d_6$) δ 9.91 (bs, 1H), 9.47 (s, 1H), 7.9–8.1 (m, 6H), 7.48 (m, 1H), 7.26 bd, 1H), 7.12 (t, 1H), 6.99 (t, 1H), 6.75 (m, 1H), 6.58 (t, 1H), 6.52 (dd, 1H), 6.42 (dd, 1H), 1.98 (s, 3H); MS (ESI) 562 (M–H)$^-$.

EXAMPLE 6B

N-(3-{[(9-(Hydroxyimino)-7-{[(3-hydroxyphenyl)amino]sulfonyl}-9H-fluoren-2-yl)sulfonyl]amino}phenyl)acetamide The product from Example 6A (223 mg, 0.396 mmol) in pyridine (3 mL) was treated with hydroxylamine hydrochloride (30 mg, 0.435 mmol) and heated at reflux. After 30 minutes, the mixture was allowed to cool to ambient temperature and partitioned between ethyl acetate and $H_2O$. The separated organic phase was washed with 1 N HCl, brine, dried ($Na_2SO_4$), filtered, and the filtrate concentrated under reduced pressure. The residue was purified by flash chromatography (75% ethyl acetate/hexanes) to provide the title compound as a light yellow solid (91 mg, 40% yield). $^1$H NMR (300 MHz, DMSO-$d_6$) δ 13.32 (bs, 1H), 10.2–10.4 (bs, 2H), 9.89 (s, 1H), 9.43 (d, 1H), 8.75 (m, 1H), 8.03–8.17 (m, 3H), 7.8–7.95 (m, 2H), 7.45 (m, 1H), 7.25 (m, 1H), 7.1 (m, 1H), 6.98 (m, 1H), 6.75 (m, 1H), 6.58 (m, 1H), 6.52 (m, 1H), 6.4 (m, 1H), 1.98 (s, 3H); MS (ESI) 577 (M–H)$^-$.

EXAMPLE 7

N-(3-Aminophenyl)-9-(hydroxyimino)-N'-(3-hydroxyphenyl)-9H-fluorene-2,7-disulfonamide

EXAMPLE 7A

N-(3-Aminophenyl)-N'-(3-hydroxyphenyl)-9-oxo-9H-fluorene-2,7-disulfonamide

The product from Example 6A (289 mg, 0.554 mmol) in THF:MeOH (1:1, 20 mL) and 15% aq NaOH (10 mL) was heated at reflux. After 24 hours, the volatiles were evaporated at reduced pressure and the residue was partitioned between ethyl acetate and saturated NaHCO$_3$. The separated aqueous phase was extracted with ethyl acetate. The combined organic extracts were washed with brine, dried (Na$_2$SO$_4$), filtered, and the filtrate concentrated under reduced pressure. The residue was purified by flash chromatography (80% ethyl acetate/hexanes) to provide the title compound as an orange solid (172 mg, 55% yield). $^1$H NMR (300 MHz, DMSO-d$_6$) δ 9.50 (1H), 7.97–8.1 (m, 4H), 7.92 (d, 2H), 7.00 (t, 1H), 6.83 (t, 1H), 6.58 (t, 1H), 6.53 (m, 1H), 6.42 (m, 1H), 6.35 (t, 1H), 6.22 (m, 2H), 5.14 (bs, 2H). MS (ESI) 520 (M–H)$^-$.

EXAMPLE 7B

N-(3-Aminophenyl)-9-(hydroxyimino)-N'-(3-hydroxyphenyl)-9H-fluorene-2,7-disulfonamide The product from Example 7A (134 mg, 0.257 mmol) in pyridine (3 mL) was treated with hydroxylamine hydrochloride (20 mg, 0.283 mmol) and stirred at ambient temperature. After 3 hours, the mixture was partitioned between ethyl acetate and 1N HCl. The separated organic phase was washed with 1N HCl, saturated NaHCO$_3$, brine, dried (Na$_2$SO$_4$), filtered, and the filtrate concentrated under reduced pressure. The residue was dissolved in a minimum amount of ethyl acetate and CH$_2$Cl$_2$ was added to effect precipitation. The solid was collected by filtration and dried under reduced pressure to provide the title compound as a white solid (123 mg, 89% yield). $^1$H NMR (300 MHz, DMSO-d$_6$) δ 13.43 (bs, 1H), 10.17–10.35 (m, 1H), 9.96–10.13 (m, 1H), 9.46 (d, 1H), 8.76 (d, 1H), 8.02–8.18 (m, 3H), 7.8–7.93 (m, 2H), 6.98 (m, 1H), 6.81 (m, 1H), 6.5–6.6 (m, 2H), 6.32–6.44 (m, 2H), 6.16–6.28 (m, 2H), 5.1 (bs, 2H); MS (ESI) 535 (M–H)$^-$.

EXAMPLE 8

9-(Hydroxyimino)-N,N'-bis(3-hydroxyphenyl)-N-methyl-9H-fluorene-2,7-disulfonamide

EXAMPLE 8A 3-(Methylamino)phenol

3-Aminophenol (5.37 g, 49.2 mmol) in ethylformate (30 mL) was treated with p-toluenesulfonic acid (50 mg) and heated at reflux. After 18 hours, the volatiles were evaporated under reduced pressure. The residue was taken up in ethyl acetate and washed with 1N HCl, saturated NaHCO$_3$, brine, dried (Na$_2$SO$_4$), filtered, and the filtrate concentrated under reduced pressure. The residue was dissolved in THF (25 mL) and treated with 1M borane tetrahydofuran complex (27.2 mL, 27.2 mmol) in THF. After 18 hours at ambient temperature, the mixture was carefully quenched by addition of 1N HCl. After stirring for 30 minutes, the solution was basified and extracted with ethyl acetate. The organic layer was separated, washed with brine, dried (Na$_2$SO$_4$), filtered, and the filtrate concentrated under reduced pressure. The residue was purified by flash chromatography (30% ethyl acetate/hexanes) to provide the title compound as a viscous yellow oil (1.72 g, 28% yield). $^1$H NMR (300 MHz, CDCl$_3$) δ 7.03 (t, 1H), 6.13–6.24 (m, 2H), 6.11 (t, 1H), 4.54 (bs, 1H), 3.72 (bs, 1H), 2.82 (s, 3H); MS (DCI/NH$_3$) 124 (M+H)$^+$, 141 (M$^+$NH$_4$)$^+$.

EXAMPLE 8B

N,N'-bis(3-Hydroxyphenyl)-N-methyl-9-oxo-9H-fluorene-2,7-disulfonamide

The product from Example 8A and 3-aminophenol were processed as described in Example 6A to provide the title compound. $^1$H NMR (300 MHz, DMSO-d$_6$) δ 10.29 (bs, 1H), 9.58 (bs, 1H), 9.48 (bs, 1H), 8.12 (m, 2H), 8.04 (dd, 1H), 7.95 (d, 1H), 7.80 (dd, 1H), 7.58 (d, 1H), 7.11 (t, 1H), 7.01 (t, 1H), 6.71 (m, 1H), 6.60 (t, 1H), 6.49–6.58 (m, 3H), 6.44 (m, 1H), 3.13 (s, 3H); MS (ESI) 535 (M–H)$^-$.

EXAMPLE 8C 9-(Hydroxyimino)-N,N'-bis(3-hydroxyphenyl)-N-methyl-9H-fluorene-2,7-disulfonamde The product from Example 8B was processed as described in Example 7B to provide the title compound. $^1$H NMR (300 MHz, DMSO-d$_6$) δ 9.58 (s, 1H), 9.47 (d, 1H), 7.62–8.78 (m, 6H), 7.1 (m, 1H), 6.99 (m, 1H), 6.68 (m, 1H), 6.47–6.62 (m, 4H), 6.41 (m, 1H), 3.11 (s, 3H); MS (ESI) 550 (M–H)$^-$.

EXAMPLE 9

N,N'-bis(3-Hydroxyphenyl)-9-(methylhydrazono)-9H-fluorene-2,7-disulfonamide

The product from Example 1A (0.5 g, 0.94 mmol) in EtOH (5 mL) was treated with methylhydrazine (0.06 mL, 1.1 mmol), and a catalytic amount of TsOH. The mixture was refluxed for 3 hours, allowed to cool to room temperature, concentrated under reduced pressure, and the residue was purified by flash chromatography (CH$_2$Cl$_2$:MeOH, 98:2) to provide the title compound as a yellow foam (0.3 g, 58% yield).

$^1$H-NMR (DMSO-d$_6$) δ 10.15 (broad s, 2H), 9.40 (d, J=6 Hz, 2H), 8.85 (d, 3.5 Hz, 1H), 8.60 (d, J=0.5 Hz, 1H), 8.18 (d, J=7.5 Hz, 1H), 8.06 (d, J=7.5 Hz, 1H), 7.72–7.63 (m, 2H), 6.95 (m, 2H), 6.60–6.50 (m, 4H), 6.38 (m, 2H), 3.32 (s, 3H); MS (APCI) m/z 551 (M+H)$^+$.

EXAMPLE 10

N,N'-bis(3-Hydroxyphenyl)-9,10-dioxo-9,10-dihydro-2,7-anthracenedisulfonamide

EXAMPLE 10A 9,10-Dioxo-9,10-dihydro-2,7-anthracenedisulfonyl Dichloride

Anthraquinone-2,7-disulfonic acid disodium salt (1.24 g, 3 mmol) and sulfolane (5 ml) in acetonitrile (5 ml) was treated with phosphorous oxychloride (2.3 ml, 25 mmol). The mixture was heated at reflux for 20 hours, allowed to cool to room temperature, and filtered through a pad of silica gel with methylene chloride. The filtrate was concentrated under reduced pressure and the crude product was used in the next step without further purification.

EXAMPLE 10B

N,N'-bis(3-Hydroxyphenyl)-9,10-dioxo-9,10-dihydro-2,7-anthracenedisulfonamide 3-aminophenol (0.76 g, 7 mmol) in pyridine (10 ml) was treated with the product from Example 10A in methylene chloride. The mixture was stirred at room temperature for 18 hours and the solvents removed under reduced pressure. The residue was taken up in ethyl acetate, washed three times with 1N hydrochloric acid, dried with magnesium sulfate, filtered, and the filtrate concentrated under reduced pressure. The residue was filtered through a pad of silica gel with 5% methanol in methylene chloride. The filtrate was concentrated under reduced pressure and the residue was taken up in a mixture of ethyl acetate:hexanes (1:1). The mixture was washed three times with water, dried with magnesium sulfate, filtered, and the filtrate concentrated under reduced pressure. The residue was titurated with methylene chloride and the orange solid collected by filtration to provide the title compound (0.47 g, 28% yield for 2 steps). $^1$H NMR (CD$_3$OD) δ 7.16 (d, 2H, J=1.5 Hz), 6.86 (d, 2H, J=6 Hz), 6.69 (dd, 2H, J$_1$=6 Hz, J$_2$=1.5 Hz), 5.55–5.47 (m, 2H), 5.20–4.95 (m, 6H); MS (ESI–) 549 (M–H)$^-$.

EXAMPLE 11

10-(Hydroxyimino)-N,N'-bis(3-hydroxyphenyl)-9-oxo-9,10-dihydro-2,7-anthracenedisulfonamide The product from Example 10B (110 mg, 0.2 mmol) and hydroxylamine hydrochloride (0.69 g, 10 mmol) were dissolved in methanol (6 ml) and heated at reflux for 18 hours. The mixture was allowed to cool to room temperature and the methanol was removed under reduced pressure. The residue was taken up in water, extracted with 10% methanol in methylene chloride, the aqueous layer was brought to pH 7 with aqueous sodium bicarbonate, and extracted again with ethyl acetate. All the organic layers were combined, dried with magnesium sulfate, filtered, and the filtrate concentrated under reduced pressure. The residue was purified by flash chromatography eluting with 5% methanol in methylene chloride, followed by preparative thin-layer chromatography eluting with 10% methanol in methylene chloride to provide the title compound (20 mg, 18% yield) and the bis(oxime) (28 mg, 24% yield). $^1$H NMR (CD$_3$OD) δ 9.37 (d, 1H, J=7 Hz), 8.73 (d, 1H, J=2 Hz), 8.61 (d, 1H, J=2 Hz), 8.41 (d, 1H), J=7 Hz), 8.08 (dd, 1H, J$_1$=7 Hz, J$_2$=2 Hz), 7.96 (dd, 1H, J$_1$=7 Hz, J$_2$=2 Hz), 7.00–6.95 (m, 2H), 6.63 (narrow m, 2H), 8.10–8.05 (m, 2H), 7.98–7.94 (m, 2H); MS (ESI+) 566 (M+H)$^+$.

EXAMPLE 12

9,10-bis(Hydroxyimino)-N,N'-bis(3-hydroxyphenyl)-9,10-dihydro-2,7-anthracenedisulfonamide The title compound was isolated as one of the products from Example 11. $^1$H NMR (CD$_3$OD) δ 9.24 and 9.19 (2d, 1H, J=2 Hz), 8.83 and 8.75 (2d, 1H, J=6 Hz), 8.44 and 8.35 (2d, 1H, J=2 Hz), 8.07 and 7.97 (2d, 1H, J=7 Hz), 7.87–7.69 (m, 2H), 7.02–6.94 (m, 2H), 6.66–6.44 (m, 6H); MS (ESI+) 581 (M+H)$^+$.

EXAMPLE 13

N,N'-bis(3-Hydroxyphenyl)-9,10-dioxo-9,10-dihydro-2,6-anthracenedisulfonamide

EXAMPLE 13A 9,10-Dioxo-9,10-dihydro-2,6-anthracenedisulfonyl Dichloride

Anthraquinone-2,6-disulfonic acid disodium salt was processed as described in Example 10A to provide the title compound.

EXAMPLE 13B

N,N'-bis(3-Hydroxyphenyl)-9,10-dioxo-9,10-dihydro-2,6-anthracenedisulfonamide

The product from Example 13A was processed as described in Example 10B to provide the title compound. $^1$H NMR (CD$_3$OD) 8.49 (d, 2H, J=1 Hz), 8.23 (d, 2H, J=6 Hz), 8.05 (dd, 2H, J$_1$=6 Hz, J$_2$=1 Hz), 6.90–6.81 (m, 2H), 6.54–6.30 (m, 6H); MS (ESI–) 549 (M–H)$^-$.

EXAMPLE 14

10-(Hydroxyimino)-N,N'-bis(3-hydroxyphenyl)-9-oxo-9,10-dihydro-2,6-anthracenedisulfonamide The product from Example 13B was processed as described in Example 11 to provide the title compound. $^1$H NMR (CD$_3$OD) δ 9.68 and 8.58 (2d, 1H, J=3 Hz), 9.32 and 8.27 (2d, 1H, J=8 Hz), 8.73 and 8.71 (2d, 1H, J=3 Hz), 8.42 and 8.39 (2d, 1H, J=8 Hz), 8.10 and 7.89 (2dd, 1H, J$_1$=8 Hz, J$_2$=3 Hz), 8.01 and 7.97 (2dd, 1H, J$_1$=9 Hz, J$_2$=3 Hz), 7.02–6.97 (m, 2H), 6.66–6.62 (m, 2H), 6.59–6.53 (m, 2H), 6.50–6.45 (m, 2H); MS (ESI–) 564 (M–H)$^-$.

EXAMPLE 15

9,10-bis(Hydroxyimino)-N,N'-bis(3-hydroxyphenyl)-9,10-dihydro-2,6-anthracenedisulfonamide The product from Example 13B was processed as described in Example 11 to provide the title compound. $^1$H NMR (CD$_3$OD) 9.21, 9.17, 8.33, 8,42 (4d, 2H, J=2 Hz), 8.85, 8.78, 8.09, 7.98 (4d, 2H, J=6 Hz), 7.85, 7.78, 7.72 (3dd, 2H, J$_1$=2 Hz, J$_2$=6 Hz), 7.01–6.95 (m, 2H), 6.65–6.61 (m, 2H), 6.57–6.45 (m, 4H); MS (ESI+) 581 (M+H)$^+$.

EXAMPLE 16

3-Methoxy-N-(7-{[(3-methoxyphenyl)sulfonyl]amino}-9-oxo-9H-fluoren-2-yl)benzenesulfonamide

EXAMPLE 16A 2,7-Diamino-9H-fluoren-9-one

The title compound was prepared according to the procedure described in P. J. Perry, M. A. Read, R. T. Davies, S. M. Gowan, A. P. Reszka, A. A. Wood, L. R. Kelland, S. Neidle, J. Med. Chem. 1999, 42, 2679.

EXAMPLE 16B

3-Methoxy-N-(7-{[(3-methoxyphenyl)sulfonyl]amino}-9-oxo-9H-fluoren-2-yl)benzenesulfonamide 3-Methoxybenzenesulfonyl chloride (4.75 g, 23.0 mmol) in THF (40 mL) was treated with the product from Example 16A (5.05 g, 24 mmol) in THF (60 mL) and pyridine (60 mL) over 10 minutes. After an additional 30 minutes, the mixture was quenched with a mixture of 1.0M (pH 6) aqueous potassium phosphate buffer (30 mL) and brine (20 mL). The aqueous phase was separated and extracted with diethyl ether. The organic phases were combined, washed 1.0M (pH 6) aqueous potassium phosphate buffer (10 mL) and brine (10 mL), and the aqueous phase was extracted with diethyl ether. All the organic phases were combined, dried (Na$_2$SO$_4$), concentrated, and the filtrate concentrated under reduced pressure. The residue was purified by flash chromatography (ethyl acetate/CH$_2$Cl$_2$). The appropriate fractions were concentrated, dissolved in a small quantity of hot methanol and triturated with diethyl ether. The resulting precipitate was collected by filtration and washed with (10% methanol/diethyl ether) to provide the title compound as an orange powder (3.51 g). 1H HNMR (DMSO-d$_6$) δ 10.55 (bs, 2H), 7.53 (d, J=8.5 Hz, 2H), 7.47 (t, J=8.0 Hz, 2H), 7.33 (d, J=7.6 Hz, 2H), 7.28–7.24 (m, 6H), 7.18 (dd, J=8.5, 2.1, 2H), 3.77 (s, 6H); MS calculated for (M+H): 550.0868; observed: 550.0848; IR 3232, 2971, 1719, 1599, 1466, 1256, 1155.

EXAMPLE 17

3-Hydroxy-N-(7-{[(3-hydroxyphenyl)sulfonyl] amino}-9-oxo-9H-fluoren-2-yl)benzenesulfonamide The product from Example 16 (551 mg, 1.00 mmol) in $CH_2Cl_2$ was treated with $BBr_3$ (~475 µL, 5.0 mmol). After 2.5 hours, additional $BBr_3$ (~235 µL, 2.5 mmol) was added to the mixture. After an additional 40 minutes, the mixture was poured onto ice-cold 0.3M (pH 6) aqueous potassium phosphate buffer (100 mL), diluted with ethyl acetate (100 mL). The organic phase was separarted, dried ($Na_2SO_4$), concentrated, filtered, and the filtrate was slurried in $CH_2Cl_2$ to provide a precipitate which was twice chromatographed ($CH_3CN/CH_2Cl_2$) to provide the title compound as an orange powder (327 mg). $^1$H HNMR ($CD_3OD$) δ 7.35–7.27 (m, 6H), 7.24 (dt, J=7.6, 1.3), 7.19–7.16 (m, 4H), 6.97 (ddd, J=7.9, 2.5, 1.3, 2H); MS calculated for (M+H): 522.0555; observed: 522.0560; IR 3457, 3346, 3232, 1718, 1604, 1468, 1311, 1150.

EXAMPLE 18

3-Hydroxy-N-(9-(hydroxyimino)-7-{[(3-hydroxyphenyl)sulfonyl]amino}-9H-fluoren-2-yl) benzenesulfonamide The product from Example 17 was processed according to the procedure described in S. Witek, J. Bielawski, A. Bielawska, Pol. J. Chem. 1981, 55, 2589, to provide the title compound. $^1$H NMR ($CD_3OD/CDCl_3$) δ 8.08 (d, J=2.4, 1H), 7.39 (d, J=2.0, 1H), 7.38 (d, J=8.1, 1H), 7.35 (d, J=8.1, 1H), 7.25–7.20 (m, 6H), 7.17 (dd, J=8.1, 2.0, 1H), 7.11 (dd, J=8.1, 2.0, 1H), 6.97–6.93 (m, 2H); MS calculated for (M+H): 537.0664; observed: 537.0671; IR 3397, 3260, 1702, 1589, 1464, 1307, 1154.

In Vitro Data

Determination of Inhibition Potencies

Compounds of the present invention were determined to be $P2X_3$ and $P2X_{2/3}$ antagonists based on their ability to inhibit increases in cytosolic $Ca^{2+}$ concentration elicited by the P2X receptor agonist αβ-methyleneATP (αβ-meATP; Sigma, St. Louis, Mo.) as described in Bianchi et al. (1999). The fluorescent $Ca^{2+}$ chelating dye fluo-4 was used as an indicator of the relative levels of intracellular $Ca^{2+}$ in a 96-well format using a Fluorescence Imaging Plate Reader (FLIPR, Molecular Devices, Sunnyvale, Calif.). Cells expressing recombinant human $P2X_3$ or $P2X_{2/3}$ containing receptors were grown to confluence and plated in 96-well black-walled tissue culture plates approximately 18 hours prior to the experiment. One to two hours before the assay, cells were loaded with fluo-4 AM (2.28 µM; Molecular Probes, Eugene, Oreg.) in D-PBS and maintained in a dark environment at room temperature. Immediately before the assay, each plate was washed twice with 250 µl D-PBS per well to remove extracellular fluo-4 AM and then 100 µl D-PBS was added to the wells. Two 50 µl additions of compounds (4x concentration prepared in D-PBS) were made to the cells during each experiment. The first addition consisting of test antagonist was made and incubation continued for 3 minutes before the addition of the agonist αβ-meATP, measurement continued for 3 minutes after this final addition. Fluorescence data was collected at 1 or 5 second intervals throughout the course of each experiment and were analyzed based on the peak increase in relative fluorescence units compared with basal fluorescence. Antagonist concentration-response data, expressed as a percentage of the maximal αβ-meATP response in the absence of test antagonist, were analyzed using GraphPad Prism (San Diego, Calif.).

The compounds of the present invention were found to be antagonists of the $P2X_3$ containing receptor with potencies from 5000 nM to 10 nM. In a preferred embodiment, the compounds of the present invention antagonized $P2X_3$ containing receptors with potencies of less than 1000 nM. In a more preferred embodiment, the compounds of the present invention antagonized $P2X_3$ containing receptors with potencies of less than 500 nM.

Additionally, the compounds of the present invention were found to be antagonists of the $P2X_{2/3}$ containing receptors with potencies from 5000 nM to 10 nM. In a preferred range, the compounds of the present invention antagonized $P2X_{2/3}$ containing receptors with potencies from 1000 nM to 10 nM. In a more preferred range, the compounds of the present invention antagonized $P2X_{2/3}$ containing receptors with potencies from 500 nM to 10 nM.

In Vivo Data

Determination of Antinociceptive Effect

Following a 30-minute acclimation period to individual clear observation cages, 50 µl of a 5% formalin solution was injected subcutaneously (s.c.) into the dorsal aspect of the right hindpaw of rats (male Sprague-Dawley, 200–300 g) were then returned to the observation cages, which were suspended above mirrors. Rats, six per group, were observed for either a continuous period of 60 minutes or for periods of time corresponding to phase 1 and phase 2 of the formalin test (Abbott et al., Pain, 60 (1995) 91–102). Phase 1 of the formalin test was defined as the period of time immediately following injection of formalin until 10 minutes after the formalin injection. Effects on Phase 2 of the formalin test were determined by monitoring for the 20 minute period of time from 30 to 50 minutes following formalin injection. Nociceptive behaviors were recorded from animals during the session by observing each animal for one 60 second observation period during each 5 minute interval. Nociceptive behaviors recorded included flinching, licking or biting the injected paw.

The compounds of the present invention were found to have antinociceptive effects with potencies from 300 µmol/kg to 15 µmol/kg.

The in vitro and in vivo data demonstrates that compounds of the present invention antagonize the $P2X_3$ containing receptor, antagonize the $P2X_{2/3}$ containing receptor, and are useful for treating pain. Compounds of the present invention are thus useful for ameliorating or preventing additional disorders that are affected by the $P2X_3$ and/or the $P2X_{2/3}$ containing receptors such as bladder overactivity and urinary incontinence.

The compounds of the invention, including but not limited to those specified in the examples, are $P2X_3$ and $P2X_2/P2X_3$ containing receptor antagonists in mammals. As $P2X_3$ and $P2X_2/P2X_3$ containing receptor antagonists, the compounds of the present invention are useful for the treatment and prevention of disorders such as bladder overactivity, urinary incontinence or pain.

The ability of the compounds of the present invention, including but not limited to those specified in the examples, to treat bladder overactivity or urinary incontinence is demonstrated by Namasivayam et al., Brit. J. Urol. Int. 84L 854–860. (1999).

The ability of the compounds of the present invention, including but not limited to those specified in the examples, to treat pain is demonstrated by Cesare et al., Drug Dev. Res. 50: S01–02 (2000); Cockayne et al., Drug Dev. Res. 50: 005 (2000); Bleehen, Br. J. Pharmacol. 62:573–577 (1978); Cook et al., Nature 387:505–508 (1997); and Driessen and Starke, Naunyn Schmiedebergs Arch. Pharmacol. 350:618–625 (1994).

The present invention also provides pharmaceutical compositions that comprise compounds of the present invention. The pharmaceutical compositions comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood.

The present invention contemplates compounds of formula I formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 100 mg/kg/day. For purposes of oral administration, more preferable doses can be in the range of from about 0.1 to about 25 mg/kg/day. If desired, the effective daily dose can be divided into multiple doses for purposes of administration; consequently, single dose compositions may contain such amounts or submultiples thereof to make up the daily dose.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A compound of formula (I)

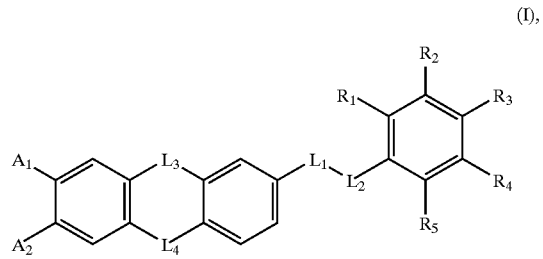

or a pharmaceutically acceptable salt, ester, amide, or prodrug thereof, wherein
$A_1$ and $A_2$ are independently selected from the group consisting of hydrogen and

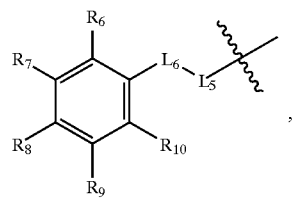

provided that one of $A_1$ and $A_2$ is hydrogen;
$L_1$ and $L_2$ are independently selected from the group consisting of $N(R_{11})$ and $S(O)_2$, provided that when $L_1$ is $N(R_{11})$ then $L_2$ is $S(O)_2$ or when $L_1$ is $S(O)_2$ then $L_2$ is $N(R_{11})$;
$L_3$ is selected from the group consisting of S, S(O), $S(O)_2$, C(O), $CH(OR_{12})$, $C(=NOR_{13})$, $C(=NNR_{12}R_{14})$, $C(=CHC(O)OR_{12})$, $CH_2$, and $CH_2CH_2$;
$L_4$ is selected from the group consisting of a covalent bond, C(O), $CH(OR_{12})$, $C(=NOR_{13})$, and $C(=NNR_{12}R_{14})$;
$L_5$ and $L_6$ are independently selected from the group consisting of $N(R_{15})$ and $S(O)_2$, provided that when $L_5$ is $N(R_{15})$ then $L_6$ is $S(O)_2$ or when $L_5$ is $S(O)_2$ then $L_6$ is $N(R_{15})$;
$R_1$, $R_2$, $R_3$, $R_4$, $R_5$, $R_6$, $R_7$, $R_8$, $R_9$, and $R_{10}$ are independently selected from the group consisting of hydrogen, alkenyl, alkoxy, alkoxycarbonyl, alkyl, alkylcarbonyl, alkylcarbonyloxy, halogen, haloalkoxy, haloalkyl, hydroxy, and $-NZ_1Z_2$ wherein $Z_1$ and $Z_2$ are independently selected from the group consisting of hydrogen, alkyl, and alkylcarbonyl;
$R_{11}$, $R_{12}$, $R_{14}$, and $R_{15}$ are independently selected from the group consisting of hydrogen and alkyl; and
$R_{13}$ is selected from the group consisting of hydrogen, alkyl, and carboxyalkyl.
2. A compound according to claim 1 wherein $A_1$ is

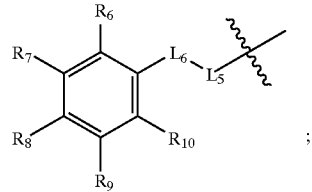

$L_1$ and $L_5$ are $-S(O)_2-$;
$L_2$ is $N(R_{11})$;

$L_6$ is $N(R_{15})$; and $L_4$ is a covalent bond.

3. A compound according to claim 2 wherein $R_1$, $R_3$, $R_4$, $R_5$, $R_6$, $R_8$, $R_9$, and $R_{10}$ are hydrogen;

$R_2$ and $R_7$ are independently selected from the group consisting of hydroxy, alkoxy, and —$NZ_1Z_2$; and $L_3$ is C(O).

4. A compound according to claim 3 selected from the group consisting of

N,N'-bis(3-hydroxyphenyl)-9-oxo-9H-fluorene-2,7-disulfonamide;

N-(3-{[(7-{[(3-hydroxyphenyl)amino]sulfonyl}-9-oxo-9H-fluoren-2-yl)sulfonyl]amino}phenyl)acetamide;

N-(3-aminophenyl)-N'-(3-hydroxyphenyl)-9-oxo-9H-fluorene-2,7-disulfonamide; and

N,N'-bis(3-hydroxyphenyl)-N-methyl-9-oxo-9H-fluorene-2,7-disulfonamide.

5. A compound according to claim 2 wherein $R_1$, $R_3$, $R_4$, $R_5$, $R_6$, $R_8$, $R_9$, and $R_{10}$ are hydrogen;

$R_2$ and $R_7$ are independently selected from the group consisting of hydroxy, alkoxy, and —$NZ_1Z_2$; and $L_3$ is C(=$NOR_{13}$).

6. A compound according to claim 5

9-(hydroxyimino)-N,N'-bis(3-hydroxyphenyl)-9H-fluorene-2,7-disulfonamide;

{[(2,7-bis{[(3-hydroxyphenyl)amino]sulfonyl}-9H-fluoren-9-ylidene)amino]oxy}acetic acid;

N-(3-{[(9-(hydroxyimino)-7-{[(3-hydroxyphenyl)amino]sulfonyl}-9H-fluoren-2-yl)sulfonyl]amino}phenyl)acetamide;

N-(3-aminophenyl)-9-(hydroxyimino)-N'-(3-hydroxyphenyl)-9H-fluorene-2,7-disulfonamide; and 9-(hydroxyimino)-N,N'-bis(3-hydroxyphenyl)-N-methyl-9H-fluorene-2,7-disulfonamide.

7. A compound according to claim 2 wherein $R_1$, $R_3$, $R_4$, $R_5$, $R_6$, $R_8$, $R_9$, and $R_{10}$ are hydrogen;

$R_2$ and $R_7$ are independently selected from the group consisting of hydroxy, alkoxy, and —$NZ_1Z_2$; and $L_3$ is C(=$NNR_{12}R_{14}$).

8. A compound according to claim 7 selected from the group consisting of 9-hydrazono-N,N'-bis(3-hydroxyphenyl)-9H-fluorene-2,7-disulfonamide; and N,N'-bis(3-hydroxyphenyl)-9-(methylhydrazono)-9H-fluorene-2,7-disulfonamide.

9. A compound according to claim 2 wherein $R_1$, $R_3$, $R_4$, $R_5$, $R_6$, $R_8$, $R_9$, and $R_{10}$ are hydrogen;

$R_2$ and $R_7$ are independently selected from the group consisting of hydroxy, alkoxy, and —$NZ_1Z_2$; and $L_3$ is CH(OR_{12}$).

10. A compound according to claim 9 that is 9-hydroxy-N,N'-bis(3-hydroxyphenyl)-9H-fluorene-2,7-disulfonamide.

11. A compound according to claim 2 wherein $R_1$, $R_3$, $R_4$, $R_5$, $R_6$, $R_8$, $R_9$, and $R_{10}$ are hydrogen;

$R_2$ and $R_7$ are independently selected from the group consisting of hydroxy, alkoxy, and —$NZ_1Z_2$; and $L_3$ is C(=CHC(O)OR_{12}$).

12. A compound according to claim 11 that is (2,7-bis{[(3-hydroxyphenyl)amino]sulfonyl}-9H-fluoren-9-ylidene) acetic acid.

13. A compound according to claim 1 wherein $A_1$ is

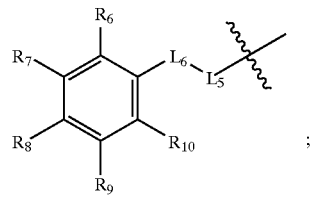

$L_1$ is $N(R_{11})$;

$L_5$ is $N(R_{15})$;

$L_2$ and $L_6$ are $S(O)_2$; and $L_4$ is a covalent bond.

14. A compound according to claim 13 wherein $R_1$, $R_3$, $R_4$, $R_5$, $R_6$, $R_8$, $R_9$, and $R_{10}$ are hydrogen;

$R_2$ and $R_7$ are independently selected from the group consisting of hydroxy, alkoxy, and —$NZ_1Z_2$; and $L_3$ is C(O).

15. A compound according to claim 14 selected from the group consisting of 3-methoxy-N-(7-{[(3-methoxyphenyl)sulfonyl]amino}-9-oxo-9H-fluoren-2-yl)benzenesulfonamide;

3-hydroxy-N-(7-{[(3-hydroxyphenyl)sulfonyl]amino}-9-oxo-9H-fluoren-2-yl)benzenesulfonamide; and 3-hydroxy-N-(9-(hydroxyimino)-7-{[(3-hydroxyphenyl)sulfonyl]amino}-9H-fluoren-2-yl)benzenesulfonamide.

16. A compound according to claim 1 wherein $A_1$ is

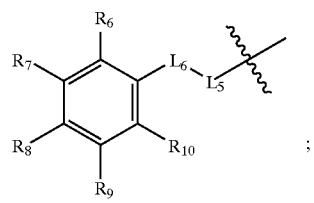

$L_1$ and $L_5$ are $S(O)_2$;

$L_2$ is $N(R_{11})$;

$L_6$ is $N(R_{15})$;

$L_3$ and $L_4$ are independently selected from the group consisting of C(O) and C(=$NOR_{13}$); and $R_{13}$ is hydrogen.

17. A compound according to claim 16 wherein $R_1$, $R_3$, $R_4$, $R_5$, $R_6$, $R_8$, $R_9$, and $R_{10}$ are hydrogen; and $R_2$ and $R_7$ are independently selected from the group consisting of hydroxy, alkoxy, and —$NZ_1Z_2$.

18. A compound according to claim 17 selected from the group consisting of

N,N'-bis(3-hydroxyphenyl)-9,10-dioxo-9,10-dihydro-2,7-anthracenedisulfonamide;

10-(hydroxyimino)-N,N'-bis(3-hydroxyphenyl)-9-oxo-9,10-dihydro-2,7-anthracenedisulfonamide; and 9,10-bis(hydroxyimino)-N,N'-bis(3-hydroxyphenyl)-9,10-dihydro-2,7-anthracenedisulfonamide.

19. A compound according to claim 1 wherein $A_2$ is

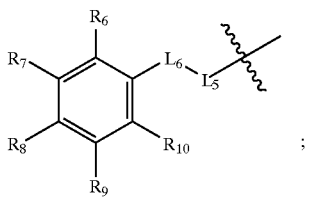

$L_1$ and $L_5$ are $S(O)_2$;
$L_2$ is $N(R_{11})$;
$L_6$ is $N(R_{15})$;
$L_3$ and $L_4$ are independently selected from the group consisting of $C(O)$ and $C(=NOR_{13})$; and
$R_{13}$ is hydrogen.

20. A compound according to claim 19 wherein
$R_1$, $R_3$, $R_4$, $R_5$, $R_6$, $R_8$, $R_9$, and $R_{10}$ are hydrogen; and
$R_2$ and $R_7$ are independently selected from the group consisting of hydroxy, alkoxy, and $-NZ_1Z_2$.

21. A compound according to claim 20 selected from the group consisting of
N,N'-bis(3-hydroxyphenyl)-9,10-dioxo-9,10-dihydro-2,6-anthracenedisulfonamide;
10-(hydroxyimino)-N,N'-bis(3-hydroxyphenyl)-9-oxo-9,10-dihydro-2,6-anthracenedisulfonamide; and
9,10-bis(hydroxyimino)-N,N'-bis(3-hydroxyphenyl)-9,10-dihydro-2,6-anthracenedisulfonamide.

22. A pharmaceutical composition comprising a therapeutically effective amount of a compound of formula (I) or a pharmaceutically acceptable salt thereof in combination with a pharmaceutically acceptable carrier.

23. A method of treating bladder overactivity in a mammal in need of such treatment comprising administering to the mammal a therapeutically effective amount of a compound of formula (I) or a pharmaceutically acceptable salt thereof.

24. A method of treating urinary incontinence in a mammal in need of such treatment comprising administering to the mammal a therapeutically effective amount of a compound of formula (I) or a pharmaceutically acceptable salt thereof.

25. A method of treating pain in a mammal in need of such treatment comprising administering to the mammal a therapeutically effective amount of a compound of formula (I) or a pharmaceutically acceptable salt thereof.

* * * * *